United States Patent [19]

Yanagawa

[11] Patent Number: 4,850,363
[45] Date of Patent: Jul. 25, 1989

[54] ULTRASONIC DIAGNOSTIC APPARATUS WITH MULTIPLE FOCAL LENGTHS

[75] Inventor: Yutaka Yanagawa, Tokyo, Japan

[73] Assignee: Olympus Optical Co., Ltd., Tokyo, Japan

[21] Appl. No.: 258,061

[22] Filed: Oct. 13, 1988

Related U.S. Application Data

[63] Continuation of Ser. No. 105,547, Oct. 5, 1987, abandoned.

[30] Foreign Application Priority Data

Oct. 16, 1986 [JP] Japan ................ 61-245776

[51] Int. Cl.[4] .............................................. A61B 8/00
[52] U.S. Cl. ........................... 128/660.09; 128/662.06
[58] Field of Search ........... 128/660.09, 660.1, 662.06, 128/660.01

[56] References Cited

U.S. PATENT DOCUMENTS

| | | | |
|---|---|---|---|
| 4,102,204 | 7/1978 | Kretz | 73/626 |
| 4,161,121 | 7/1979 | Zitelli et al. | 128/660 |
| 4,233,988 | 11/1980 | Dick et al. | 128/660 |
| 4,315,435 | 2/1982 | Proudian | 128/660 |
| 4,374,525 | 2/1983 | Baba | 128/662.06 |
| 4,466,443 | 8/1984 | Utsugi | 128/660 |
| 4,541,435 | 9/1985 | Saito et al. | 128/660 |
| 4,693,120 | 9/1987 | Robinson | 128/660 |

FOREIGN PATENT DOCUMENTS 61-11026  1/1986  Japan .......................... 128/660.09

*Primary Examiner*—Francis Jaworski
*Assistant Examiner*—George Manuel
*Attorney, Agent, or Firm*—Frishauf, Holtz, Goodman & Woodward

[57] ABSTRACT

First and second ultrasonic transducers having the same resonance frequency are provided at the distal end portion of an endoscope. Ultrasonic lenses having different focal lengths are mounted on first and second transducers, respectively. First and second transducers are rotated around the axis of the insertion portion and mechanically radial-scan an object to be examined. A controller supplies timing signals for driving the transducers in response to the radial-scan to a diagnostic device. The diagnostic device supplies drive pulses synchronized with the timing signals to either of first and second transducers. Ultrasonic echo signals received by first and second transducers are converted into reception signals and input to the diagnostic device. The diagnostic device synthesizes only those signals among the reception signals falling within predetermined distance ranges including focal points to form a tomographic image of the object.

7 Claims, 5 Drawing Sheets

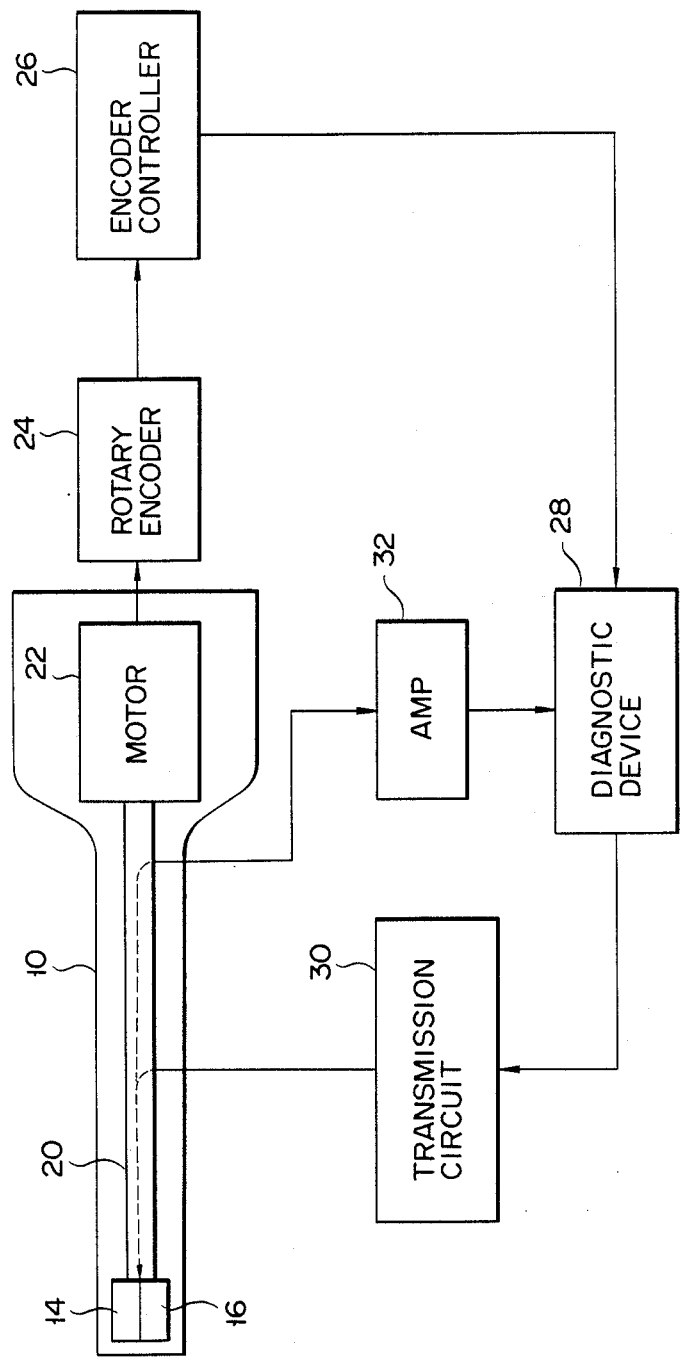
F I G. 1

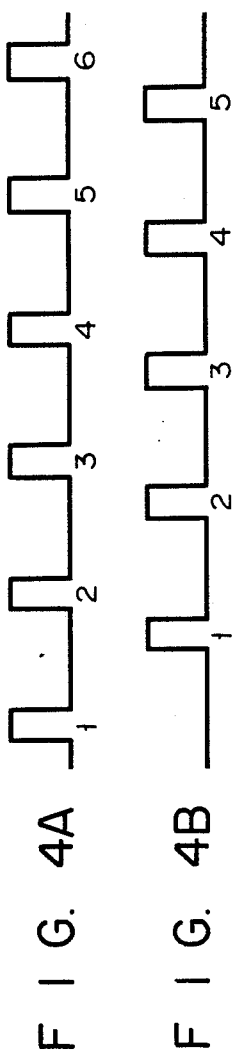
FIG. 4A
FIG. 4B
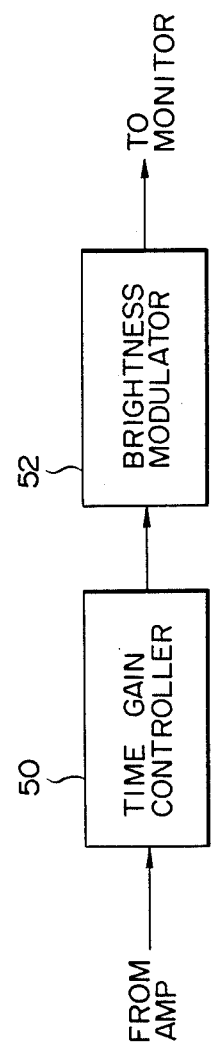
FIG. 5

ULTRASONIC DIAGNOSTIC APPARATUS WITH MULTIPLE FOCAL LENGTHS

This application is a continuation of application Ser. No. 105,547, filed Oct. 5, 1987, now abandoned.

BACKGROUND OF THE INVENTION

The present invention relates to an ultrasonic diagnostic apparatus and, more particularly, to an ultrasonic diagnostic apparatus comprising a plurality of ultrasonic transducers having different focal lengths.

In general, in an ultrasonic diagnostic apparatus, an ultrasonic transducer such as a piezoelectric element is positioned close to an object to be examined. Then, a high-frequency AC voltage of a MHz-band corresponding to a resonance frequency is applied to the transducer for an extremely short time period so that the transducer is resonated, thereby causing the transducer to emit ultrasonic pulses. In this case, if the object to be examined is a uniform medium, the ultrasonic pulses propagate straight through the medium. However, if a boundary is present between tissues having different acoustic impedances, some pulses are reflected but others are transmitted. These reflected echos are received by the transducer, and a distance between the transducer and the boundary is measured in accordance with a speed of the ultrasonic wave and a time required for the ultrasonic pulse to reciprocate. When echo signals obtained from one transmitted pulse are aligned in time sequence, an image signal representing slice information of the tissue along the transmission direction is obtained. In a radial scanning type diagnostic apparatus, the transducer is rotated in a slice of the object to be examined. Therefore, by causing the transducer to transmit ultrasonic pulses n times during each rotation, an image signal in a scanning line is obtained by dividing a circle at n equal angular intervals, thereby obtaining a tomographic image of the object to be examined.

In this case, a resonance frequency of the transducer is predetermined, and as the resonance frequency is increased, resolution is increased. However, attenuation of the ultrasonic wave is also increased, thereby shortening a distance through which the ultrasonic wave propagates. On the contrary, if the resonance frequency is low, attenuation is small, so that the ultrasonic wave can propagate over a long distance. However, since resolution is poor, diagnosis of a detailed portion cannot be performed. For this reason, in order to obtain a clear image in a wide range from short to long distances, a total distance is divided into a plurality of short distances, and a transducer having an optimal resonance frequency is assigned to each short distance, i.e., a plurality of transducers must be provided.

Such a conventional ultrasonic diagnostic apparatus is disclosed in Japanese Patent Disclosure (Kokai) No. 61-11026. This apparatus comprises a probe having at its distal end a flexible tube to be freely inserted/removed with respect to a body cavity, and two ultrasonic transducers having different resonance frequencies and incorporated in the distal end of the flexible tube. An ultrasonic lens having a short focal length is mounted on the ultrasonic transducer having a high resonance frequency, and an ultrasonic lens having a long focal length is mounted on the ultrasonic transducer having a low resonance frequency. In this apparatus, the two transducers are simultaneously driven to obtain close and remote images. Then, the close and remote images are synthesized into a single image, and this single image is displayed in real time.

However, in this conventional apparatus, the transducers having different resonance frequencies are used. Therefore, drivers having different frequencies must be provided, so that a circuit arrangement of the driver is undesirably complicated.

This problem is not limited to an intracorporeal ultrasonic diagnostic apparatus but can be applied to an extracorporeal diagnostic apparatus in which a probe is in contact with the body surface and which probe comprises transducers having different focal lengths and different resonance frequencies.

SUMMARY OF THE INVENTION

It is an object of the present invention to provide an ultrasonic diagnostic apparatus capable of obtaining an image with high resolution in a wide distance range from short to long distances by a driver having a simple arrangement.

An ultrasonic diagnostic apparatus according to the present invention comprises a plurality of transducers having the same resonance frequency and different focal lengths, a circuit for scanning the plurality of transducers, a transmission circuit for applying drive signals having the same frequency to the plurality of transducers, and a diagnostic device for synthesizing only signals among reception signals received from the plurality of transducers and falling within predetermined distance ranges including focal points to form an image therefrom.

BRIEF DESCRIPTION OF THE DRAWINGS

FIG. 1 is a block diagram of a first embodiment of an ultrasonic diagnostic apparatus according to the present invention;

FIGS. 4A and 4B are views showing waveforms of drive signals of the ultrasonic transducers of the first embodiment;

FIG. 5 is a block diagram showing a diagnostic device of the first embodiment in detail;

DETAILED DESCRIPTION OF THE PREFERRED EMBODIMENTS

Embodiments of an ultrasonic diagnostic apparatus according to the present invention will be described below with reference to the accompanying drawings.

FIG. 1 is a block diagram of a first embodiment of the present invention. Although extracorporeal and intracorporeal ultrasonic diagnostic apparatuses are available, a description in the first embodiment will be made by exemplifying an intracorporeal ultrasonic diagnostic apparatus in which an ultrasonic probe is inserted in a body cavity. However, the present invention can be similarly applied to an extracorporeal ultrasonic diagnostic apparatus.

In this embodiment, a flexible insertion portion of endoscope 10 is used as a probe, and first and second ultrasonic transducers 14 and 16 are provided at the distal end portion of the insertion portion. As an endoscope, a conventional fiber scope having an image guide fiber may be used, and a recently developed so-called electronic scope incorporating a so-called solid-state imaging element such as a CCD at its distal end portion may also be used. Although not shown, during diagnosis, the distal end portion of the insertion portion is fixed in a tube-like organ by a balloon which is filled with water. Ultrasonic lenses having different focal lengths are mounted on transducers 14 and 16, respectively. Note that transducers 14 and 16 have the same resonance frequency.

Figure 2:
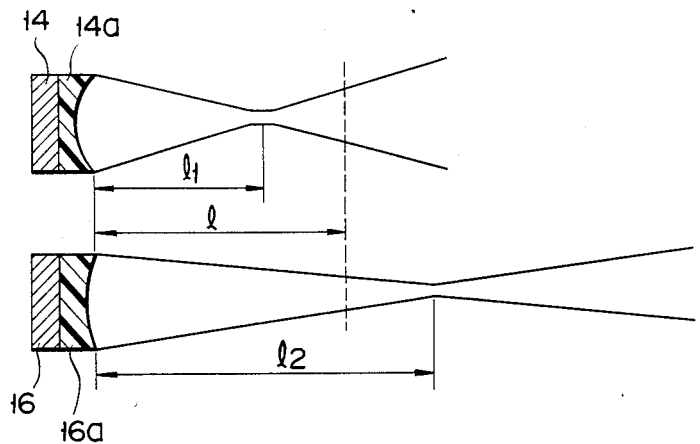
FIG. 2 is a view showing focal lengths of ultrasonic transducers of the first embodiment.

FIG. 2 is a view showing focal lengths of concave lenses 14a and 16a respectively mounted on transducers 14 and 16. In FIG. 2, focal length 11 of lens 14a of transducer 14 is shorter than focal length 12 of lens 16a of transducer 16. Distance 1 between 11 and 12 is a boundary for synthesizing images from transducers 14 and 16. In a synthetic image, an image from transducer 14 having focal length 11 which is shorter than distance 1 is used as an image inside distance 1, and an image from transducer 16 having focal length 12 which is longer than distance 1 is used as an image outside distance 1. Since a diameter of an ultrasonic beam is minimized at a focal point, highest resolution is obtained thereat. Thus, by synthesizing only images among images received from the respective transducers and falling within predetermined distance ranges including the focal points, an image with high resolution can be obtained as a whole.

Transducers 14 and 16 are rotated by motor 22 around the axis of the insertion portion through transducer fixing member 20. Assume that transducer surfaces of transducers 14 and 16 face the circumferential direction of the insertion portion. That is, transducers 14 and 16 mechanically radial-scan a slice of an object to be examined perpendicular to the axis of the insertion portion. This scanning method is merely an example, and electronic linear scanning or electronic sector scanning may be used. Moreover, a slice to be scanned may be a slice along the axis of the insertion portion. Transducers 14 and 16 are adhered back to back with each other and hence are rotated with a phase difference of 180°.

Rotary encoder 24 is connected to motor 22 and generates a synchronizing signal (a plurality of pulses/one rotation) in response to rotation of motor 22. This synchronizing signal is supplied to encoder controller 26. Controller 26 converts the input signal into pulses of TTL (transistor-transistor-logic)level, and generates timing pulses for driving the transducers in synchronism with leading or trailing edges of the TTL pulse and a positioning pulse for determining a start position of a display. These pulses are supplied to diagnostic device 28. A plurality of timing pulses are generated during each rotation of fixing member 20, and the positioning pulse is generated in synchronism with a given pulse among the timing pulses generated during one rotation.

Device 28 supplies drive pulses synchronized with the timing pulses to transmission circuit 30. Circuit 30 boosts these pulses and supplies them to either transducer 14 or 16, thereby exciting the transducer.

Ultrasonic echo signals transmitted from transducers 14 and 16, reflected by a boundary of tissues having different acoustic impedances, and received by transducers 14 and 16 are converted into reception signals and supplied to device 28 through amplifier 32. Device 28 synthesizes the signals from transducers 14 and 16, modulates brightness of the synthetic signal, and displays a tomographic image of the object to be examined on a monitor in device 28.

Figure 3:
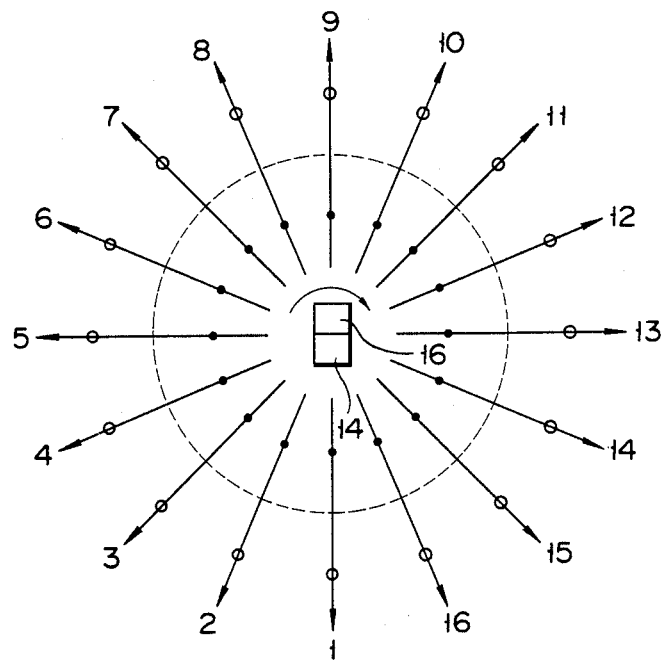
FIG. 3 is a view showing a state wherein images are synthesized according to the first embodiment.

An operation of the first embodiment will be described below. Assume that each transducer transmits/receives 16 times during one rotation of motor 22, thereby forming a frame by 16 radial scanning lines. When transducer 14 faces direction "1" in FIG. 3, transducer 14 transmits/receives ultrasonic pulses. When fixing member 20 rotates through an angle of 360°/2 (one-half revolution) and transducer 16 faces direction "1", transducer 16 transmits/receives ultrasonic pulses. When fixing member 20 rotates through an angle of (360°/2+360°/16) and transducer 14 faces direction "2", transducer 14 transmits/receives ultrasonic pulses. When fixing member 20 rotates through an angle of 360°/2 and transducer 16 faces direction "2", transducer 16 transmits/receives ultrasonic pulses, and so on. Thus, in each direction, transducers 14 and 16 alternately transmit/receive the ultrasonic pulses. In FIG. 3, black dots represent focal points of ultrasonic beams from transducer 14, and white dots represent focal points of ultrasonic beams from transducer 16. A circle represented by a broken line is a circle of a radius corresponding to distance 1 in FIG. 2. FIGS. 4A and 4B show waveforms of drive signals representing drive timings in each direction of transducers 14 and 16, respectively. Numerals under pulses represent the directions shown in FIG. 3.

FIGS. 4A and 4B respectively show the timings at which transducers 14 and 16 generate ultrasonic pulses. The pulses generated by transducers 14 and 16 are respectively shown in FIGS. 4A and 4B, and the numbers near the pulses indicate the transmission direction of the pulses. More specifically, FIGS. 4A and 4B show that, first, transducer 14 transmits a pulse in direction "1", next, transducer 16 transmits a pulse in direction "1" after a half plus 1/16 rotation of fixing member 20, then, after member 20 performs a 1/16 rotation transducer 14 transmits a pulse in direction "2", and so on.

Thus, two images are obtained from each transducer 14 or 16.

Device 28 synthesizes the images from transducers 14 and 16 as shown in FIG. 3. That is, device 28 synthesizes only an image inside distance 1 of the images from transducer 14 and only an image outside distance 1 of the images from transducer 16. This synthesis is executed by a time gain controller shown in FIG. 5. Signals from amplifier 32 supplied from device 28 are gain-controlled through time gain controller 50, supplied to brightness controller 52, and then formed into an image. Note that during formation of an image, data between the scanning lines are interpolated.

Controller 50 performs complemental time gain control (i.e., different gain control for signals from transducers 14 and 16) so that the signals from one of transducers 14 and 16 are set to be zero. In general, as for a reception signal of an ultrasonic wave, the shorter a distance becomes, the stronger a reflected signal becomes, and the longer the distance becomes, the weaker the reflected signal becomes. For this reason, if the reception signals are directly formed into an image, the relative brightness of an image portion near the transducer becomes excessively high. Therefore, as the distance is increased (a reception time is increased), gains of the reception signals are gradually increased. The present invention utilizes this technique, i.e., the gains of signals from one of the transducers are set to be zero at a certain reception time (corresponding to distance l in FIG. 2).

Figure 6A:
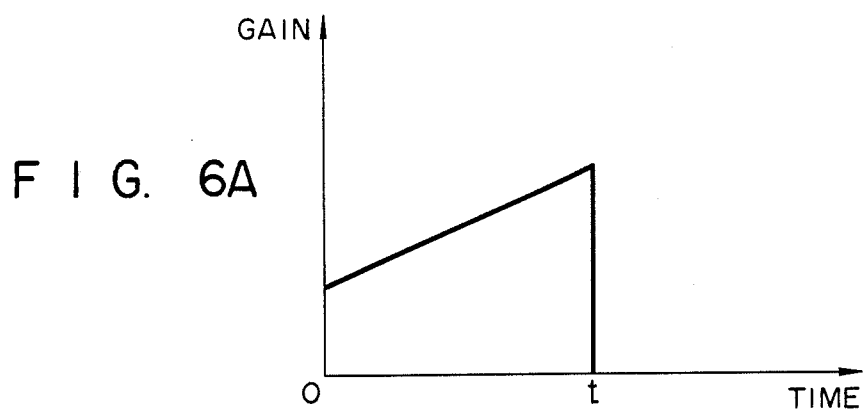
FIGS. 6A and 6B are graphs showing characteristics of a time gain controller shown in FIG. 5.
Figure 6B:
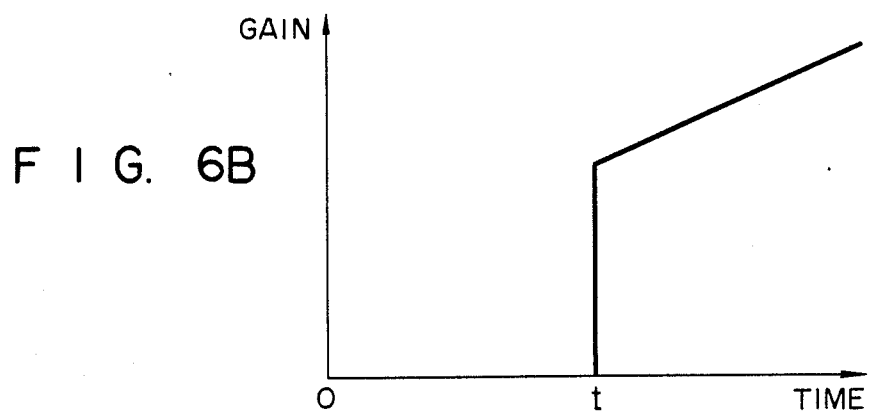

FIGS. 6A and 6B respectively show complemental time gain control curves applied to the signals from transducers 14 and 16. In FIGS. 6A and 6B, reception time t corresponds to distance l shown in FIG. 2. That is, the gain of the signal from transducer 14 is gradually increased before time t and is set to be zero thereafter. The gain of the signal from transducer 16 is set to be zero before time t and is gradually increased thereafter. Thus, the time gain control curves shown in FIGS. 6A and 6B have complementary characteristics. Note that at time t, the gain applied to the signal from transducer 14 is equal to that applied to the signal from transducer 16.

As has been described above, according to the first embodiment, in the ultrasonic diagnostic apparatus comprising a plurality of transducers having different focal lengths, a plurality of transducers have the same resonance frequency and hence can be driven by a single driver. In addition, of the signals from the respective transducers, signals near a focal point of the transducer having the highest resolution are synthesized to form an image. Therefore, there is provided an ultrasonic diagnostic apparatus capable of obtaining an image with high resolution in a wide distance range from short to long distances. Note that the number of transducers is not limited to two but may be three or more.

Figure 7:
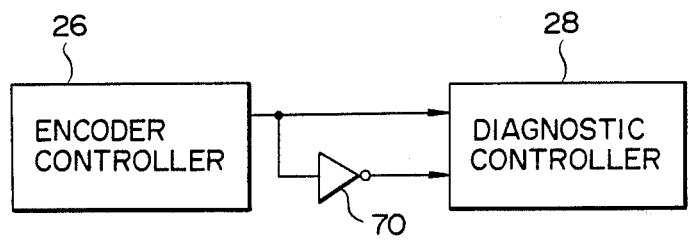
FIG. 7 is a view of main part of a second embodiment.

FIG. 7 shows the main part of a second embodiment. Timing pulses from encoder controller 26 are supplied to diagnostic device 28 either directly or through inverter 70.

An operation of the second embodiment will be described with reference to FIGS. 8 and 9. In this embodiment, transducers 14 and 16 transmit/receive ultrasonic waves in 32 directions during one rotation of motor 22, thereby forming a frame by 32 radial scanning lines twice those of the first embodiment. When transducer 14 faces direction "1" in FIG. 8, transducer 14 transmits/receives ultrasonic pulses. When transducer fixing member 20 rotates through an angle of (360°/2+360°/32) and transducer 16 faces direction "2", transducer 16 transmits/receives ultrasonic pulses. When fixing member 20 rotates through an angle of (360°/2+360°/32) and transducer 14 faces direction "3", transducer 14 transmits/receives ultrasonic pulses. When fixing member 20 rotates through an angle of (360°/2 +360°/12) and transducer 16 faces direction "4", transducer 16 transmits/receives ultrasonic pulses, and so on. Thus, unlike in the first embodiment, as fixing member 20 rotates one of transducers 14 and 16 alternately transmits/receives the ultrasonic pulses in every other direction. That is, in the first embodiment, both of transducers 14 and 16 alternately transmit/receive the ultrasonic pulses in each direction. However, in the second embodiment, only one of transducers 14 and 16 transmits/receives the ultrasonic pulses in one direction while the number of scanning lines are doubled. The number of transmissions/receptions in the first embodiment is the same as that in the second embodiment.

Figure 8:
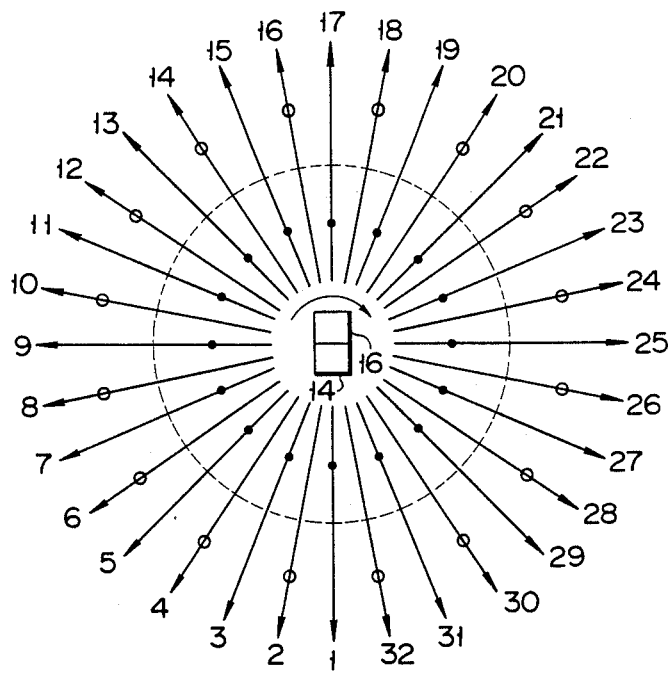
FIG. 8 is a view showing a state wherein images are synthesized according to the second embodiment.
Figure 9A:
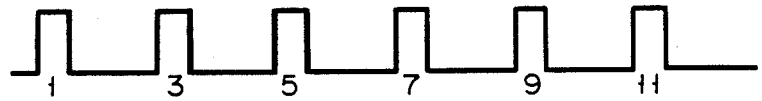
FIGS. 9A and 9B are views showing waveforms of drive signals of the ultrasonic transducers of the second embodiment.
Figure 9B:

Black dots in FIG. 8 represent focal points of transducer 14, and white dots represent focal points of transducer 16. A circle represented by a broken line is a circle of a radius corresponding to distance l of FIG. 2. FIGS. 9A and 9B are views showing waveforms representing drive timings of transducers 14 and 16, respectively. Numerals under pulses represent the directions shown in FIG. 3.

Also in the second embodiment, two images are obtained from each of transducers 14 and 16. Therefore, as in the first embodiment, by synthesizing only images falling within the range including the focal points, an image can be obtained with high resolution.

What is claimed is:

1. An ultrasonic diagnostic apparatus comprising:
a plurality of transducers having the same resonance frequency and different respective focal lengths;
scanning means for scanning said plurality of transducers such that said transducers radiate ultrasonic waves in the same plane;
driving means for applying drive signals having the same frequency to said plurality of transducers;
said plurality of transducers receiving echo signals corresponding to reflected radiated ultrasonic waves, and producing corresponding reception signals; and
synthesizing means for receiving reception signals from said plurality of transducers and for synthesizing only those reception signals from said plurality of transducers which represent distances falling within a predetermined distance range including the focal length of the respective transducer, to thereby form an image viewed in said same plane;
said synthesizing means comprising:
time gain controlling means for performing complemental time gain control of said reception signals from said plurality of transducers, said time gain controlling means including means for increasing gain during a time period corresponding to the focal length of each transducer, after the transducers have radiated ultrasonic waves; and
modulating means for modulating the output signal from said time gain controlling means to control a brightness of an image viewed in said same plane.

2. An apparatus according to claim 1, in which said scanning means scans said plurality of transducers in a given direction such that said driving means sequentially drives all of said plurality of transducers in said given direction.

3. An apparatus according to claim 1, in which said scanning means scans said plurality of transducers in a given direction such that said driving means sequentially drives at least one of said plurality of transducers in said given direction.

4. An ultrasonic diagnostic apparatus for an endoscope, comprising:
a plurality of transducers provided at a distal end of an insertion portion of an endoscope and having the same resonance frequency and different respective focal lengths, said insertion portion having an axis;
scanning means for integrally rotating said plurality of transducers in a plane perpendicular to said axis of said insertion portion of said endoscope such that said transducers radiate ultrasonic waves in the same plane;
driving means for sequentially applying drive signals having the same frequency to said plurality of transducers;

said plurality of transducers receiving echo signals corresponding to reflected radiated ultrasonic waves, and producing corresponding reception signals; and synthesizing means for receiving reception signals from said plurality of transducers and for synthesizing only reception signals from said plurality of transducers which represent distances falling within a predetermined distance range including the focal length of the respective transducer, to thereby form an image viewed in said same plane;

said synthesizing means comprising:

time gain controlling means for performing complemental time gain control of said reception signals from said plurality of transducers and for producing output signals, said time gain controlling means including means for increasing gain during a time period corresponding to the focal length of each transducer, after the transducers have radiated ultrasonic waves; and modulating means for modulating the output signals from said time gain controlling means to control a brightness of an image viewed in said same plane.

5. An apparatus according to claim 4, in which said scanning means scans said plurality of transducers in a given direction such that said driving means sequentially drives all of said plurality of transducers in said given direction.

6. An apparatus according to claim 4, in which said scanning means scans said plurality of transducers in a plurality of directions, such that said driving means sequentially drives said plurality of transducers in all of said directions and drives only one of said plurality of transducers in one of said directions.

7. An apparatus according to claim 4, in which:

the endoscope of said ultrasonic diagnostic apparatus comprises grip means;

said plurality of transducers each have transducer surfaces and respective opposite surfaces, and wherein said transducers are adhered with each other so as to be integral with each other on said surface opposite to their said transducer surfaces; and said grip means comprises said scanning means mounted thereto, said scanning means comprising a motor having a rotatable shaft coupled thereto, said rotatable shaft extending along said axis of said insertion portion, and a transmission member coupled to said rotatable shaft for transmitting a rotational force of rotatable shaft of said motor to said plurality of transducers which are adhered with each other.

* * * * *